United States Patent
Lee et al.

(10) Patent No.: US 10,384,146 B2
(45) Date of Patent: Aug. 20, 2019

(54) DIVIDED WALL DISTILLATION COLUMN

(71) Applicant: LG CHEM, LTD., Seoul (KR)

(72) Inventors: Sung Kyu Lee, Daejeon (KR); Joon Ho Shin, Daejeon (KR); Sung Kyun Kim, Daejeon (KR); Jong Ku Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 204 days.

(21) Appl. No.: 14/905,245

(22) PCT Filed: Jul. 18, 2014

(86) PCT No.: PCT/KR2014/006574
§ 371 (c)(1),
(2) Date: Jan. 14, 2016

(87) PCT Pub. No.: WO2015/009117
PCT Pub. Date: Jan. 22, 2015

(65) Prior Publication Data
US 2016/0193540 A1   Jul. 7, 2016

(30) Foreign Application Priority Data

Jul. 18, 2013 (KR) .................. 10-2013-0084495
Jul. 18, 2013 (KR) .................. 10-2013-0084496
(Continued)

(51) Int. Cl.
*B01D 3/14* (2006.01)
*B01D 3/32* (2006.01)
(Continued)

(52) U.S. Cl.
CPC ............. *B01D 3/141* (2013.01); *B01D 3/008* (2013.01); *B01D 3/143* (2013.01); *B01D 3/32* (2013.01);
(Continued)

(58) Field of Classification Search
CPC .......... B01D 3/141; B01D 3/008; B01D 3/14; B01D 3/20; B01D 3/32; B01D 3/143;
(Continued)

(56) References Cited

U.S. PATENT DOCUMENTS 4,559,108 A * 12/1985 Ahlberg ............... B01D 1/2806
202/154
5,709,780 A *  1/1998 Ognisty ................... B01D 3/14
196/99
(Continued)

FOREIGN PATENT DOCUMENTS

CN    102188831 A    9/2011
CN    102190559 A    9/2011
(Continued)

OTHER PUBLICATIONS

Porter, E. A., "Distillaiton", Feb. 10, 2011, Thermopedia. Available online at: http://www.thermopedia.com/content/703/.*

*Primary Examiner* — Jonathan Miller
*Assistant Examiner* — Jonathan Luke Pilcher
(74) *Attorney, Agent, or Firm* — Dentons US LLP

(57) ABSTRACT

Provided are a divided wall distillation column and a separating method. According to the divided wall distillation column and the separating method, when a mixture having three or more components is separated, a material to be separated, for example, 2-ethyl hexyl acrylate can be separated with high purity, and energy reduction in a separation and refinement process of 2-ethyl hexyl acrylate can be promoted.

15 Claims, 11 Drawing Sheets

(30) Foreign Application Priority Data

Sep. 5, 2013 (KR) ........................ 10-2013-0106471
Jul. 18, 2014 (KR) ........................ 10-2014-0091328

(51) Int. Cl.
*C07C 41/42* (2006.01)
*C07C 67/54* (2006.01)
*C07C 69/54* (2006.01)
*B01D 3/00* (2006.01)

(52) U.S. Cl.
CPC ................ *C07C 67/54* (2013.01); *B01D 3/14* (2013.01); *C07C 41/42* (2013.01); *C07C 69/54* (2013.01)

(58) Field of Classification Search
CPC . B01D 3/322; B01D 3/36; B01D 3/40; B01D 3/4261; B01D 3/4283; B01D 1/007; C07C 41/42; C07C 67/54; C07C 69/54
See application file for complete search history.

(56) References Cited

U.S. PATENT DOCUMENTS

| | | | |
|---|---|---|---|
| 6,294,056 B1* | 9/2001 | Matsumoto | B01D 3/008 202/158 |
| 6,348,637 B1* | 2/2002 | Harris | B01D 3/141 208/347 |
| 6,550,274 B1* | 4/2003 | Agrawal | B01D 3/14 62/617 |
| 7,556,717 B2* | 7/2009 | Heida | B01D 3/141 203/27 |
| 8,888,076 B2 | 11/2014 | Tamminen et al. | |
| 8,894,821 B2 | 11/2014 | Lee et al. | |
| 8,901,346 B2 | 12/2014 | Merenov et al. | |
| 9,724,619 B2* | 8/2017 | Bhargava | B01D 3/141 |
| 2005/0199482 A1* | 9/2005 | Heida | B01D 3/141 203/50 |
| 2006/0021911 A1* | 2/2006 | Adrian | B01D 3/141 208/115 |
| 2014/0231238 A1* | 8/2014 | Bhargava | B01D 3/141 202/161 |
| 2015/0119612 A1* | 4/2015 | Agrawal | B01D 3/141 585/16 |
| 2015/0166445 A1* | 6/2015 | Kiss | B01D 3/002 203/13 |
| 2015/0211790 A1* | 7/2015 | Bhargava | B01D 3/141 62/625 |

FOREIGN PATENT DOCUMENTS

| | | |
|---|---|---|
| CN | 101798528 B | 2/2013 |
| CN | 202921009 U | 5/2013 |
| JP | 52-62958 | 5/1977 |
| JP | 56-113717 A | 9/1981 |
| JP | 9-117602 A | 5/1997 |
| JP | 10-057704 A | 3/1998 |
| JP | 2006-509619 A | 3/2006 |
| JP | 2013-525097 A | 6/2013 |
| KR | 10-2002-0014300 A | 2/2002 |
| KR | 10-2011-0082149 A | 7/2011 |
| WO | 01/54785 A2 | 8/2001 |
| WO | 2012/091397 A2 | 7/2012 |

* cited by examiner

[Fig. 1]
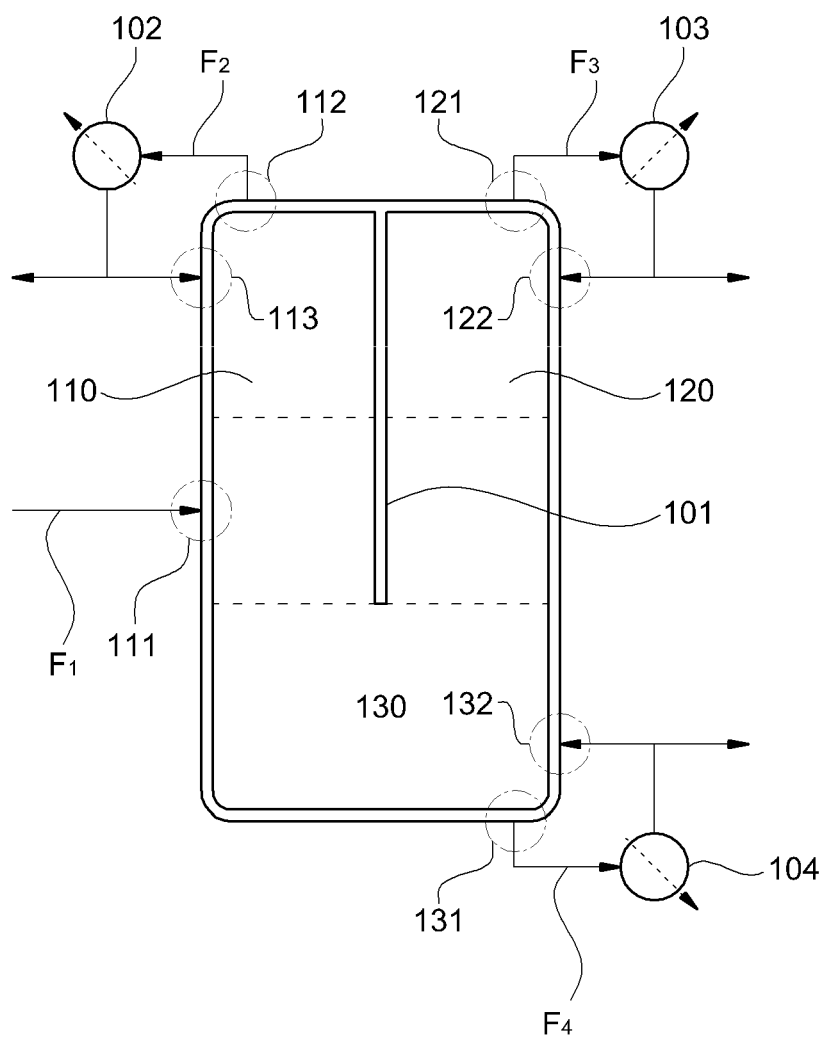

[Fig. 2]
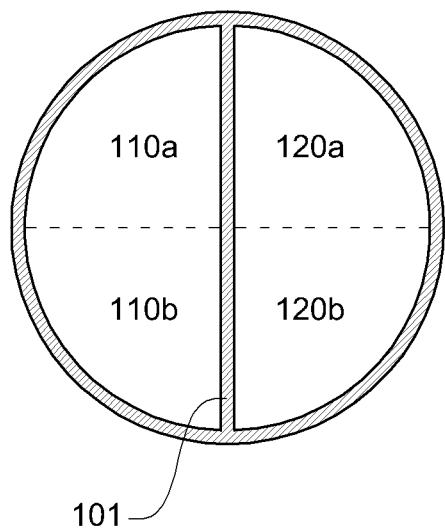
[Fig. 3]
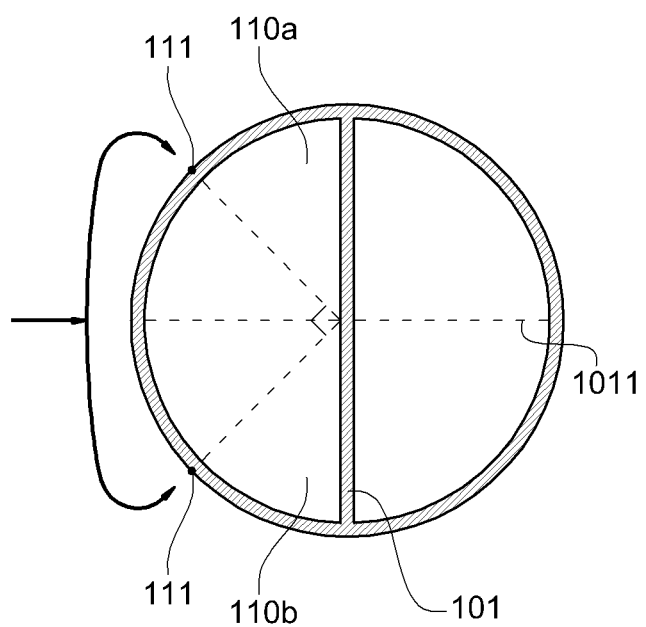

[Fig. 4]
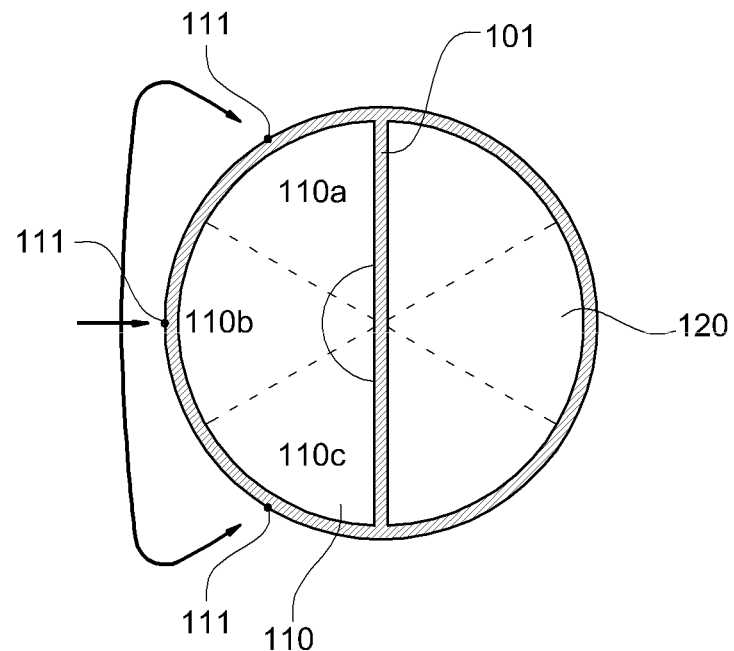
[Fig. 5]
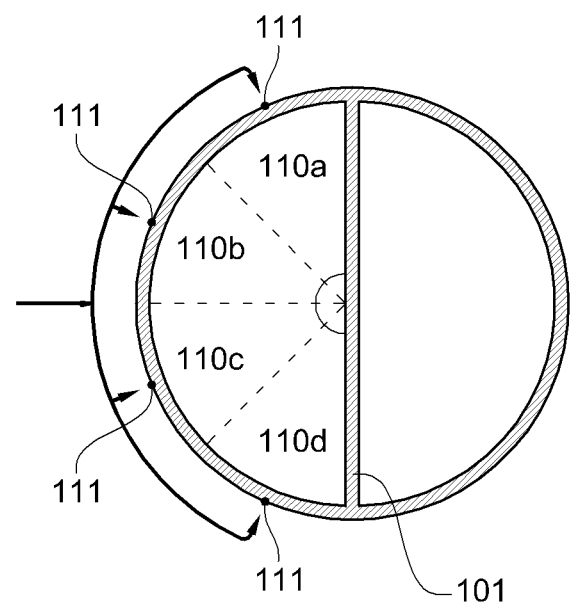

[Fig. 6]
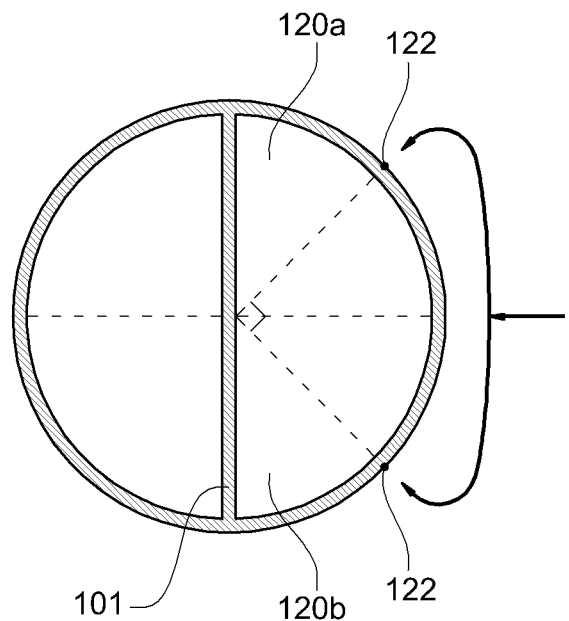
[Fig. 7]
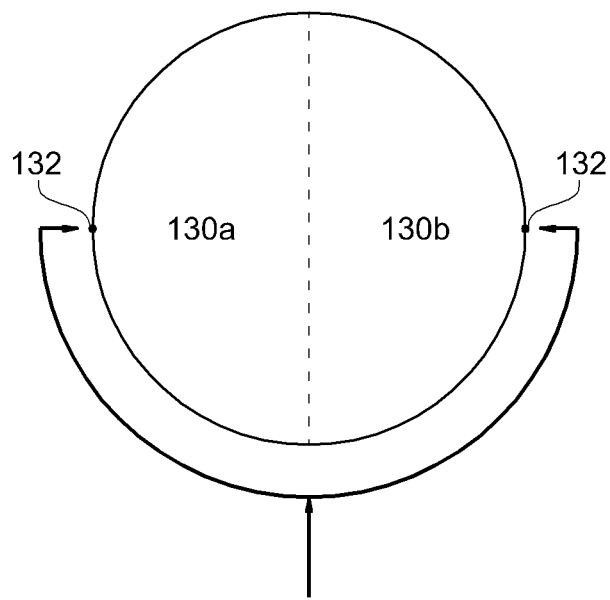

[Fig. 8]
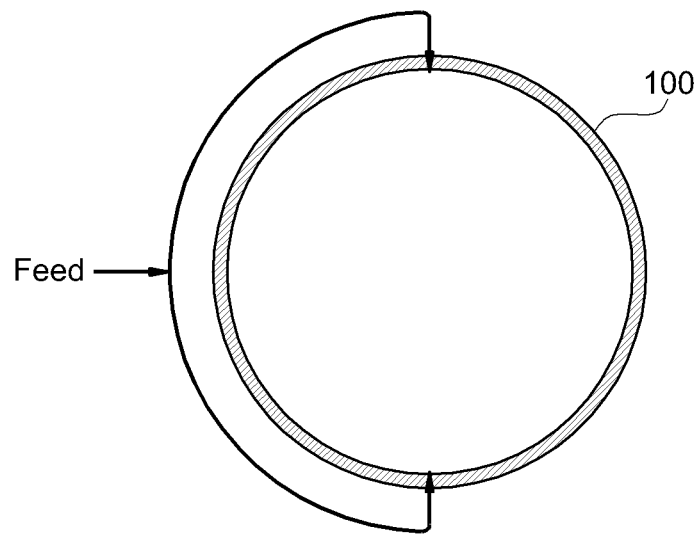
Feed
[Fig. 9]
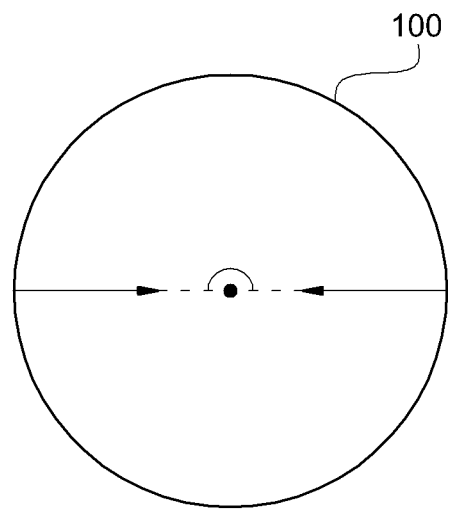

[Fig. 10]
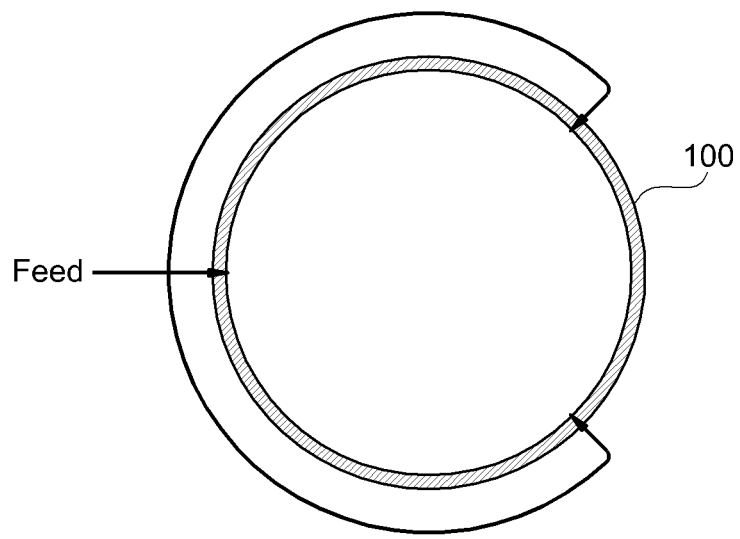
Feed
100
[Fig. 11]
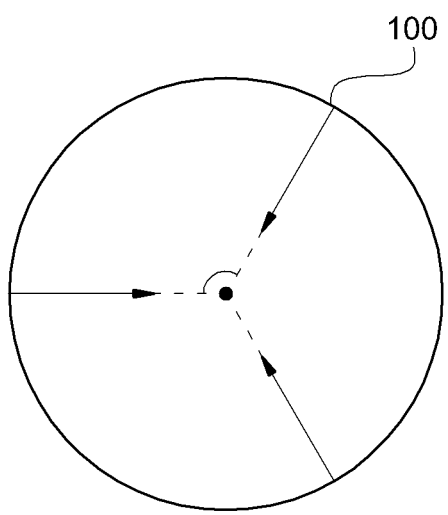
100

[Fig. 12]
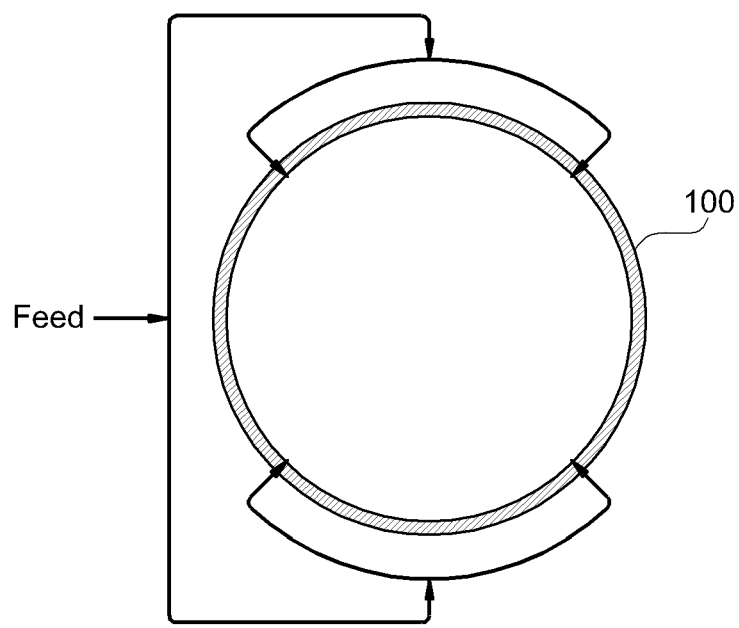
Feed
100
[Fig. 13]
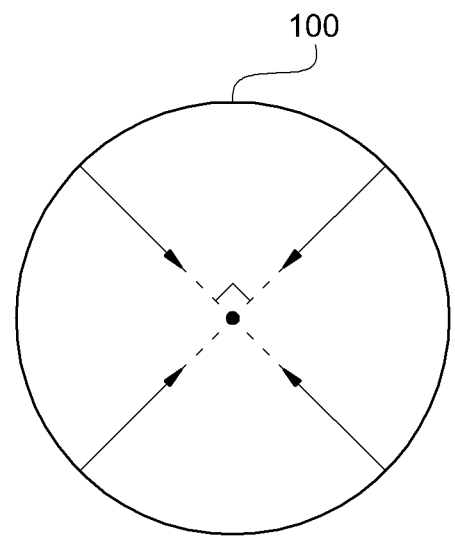
100

[Fig. 14]
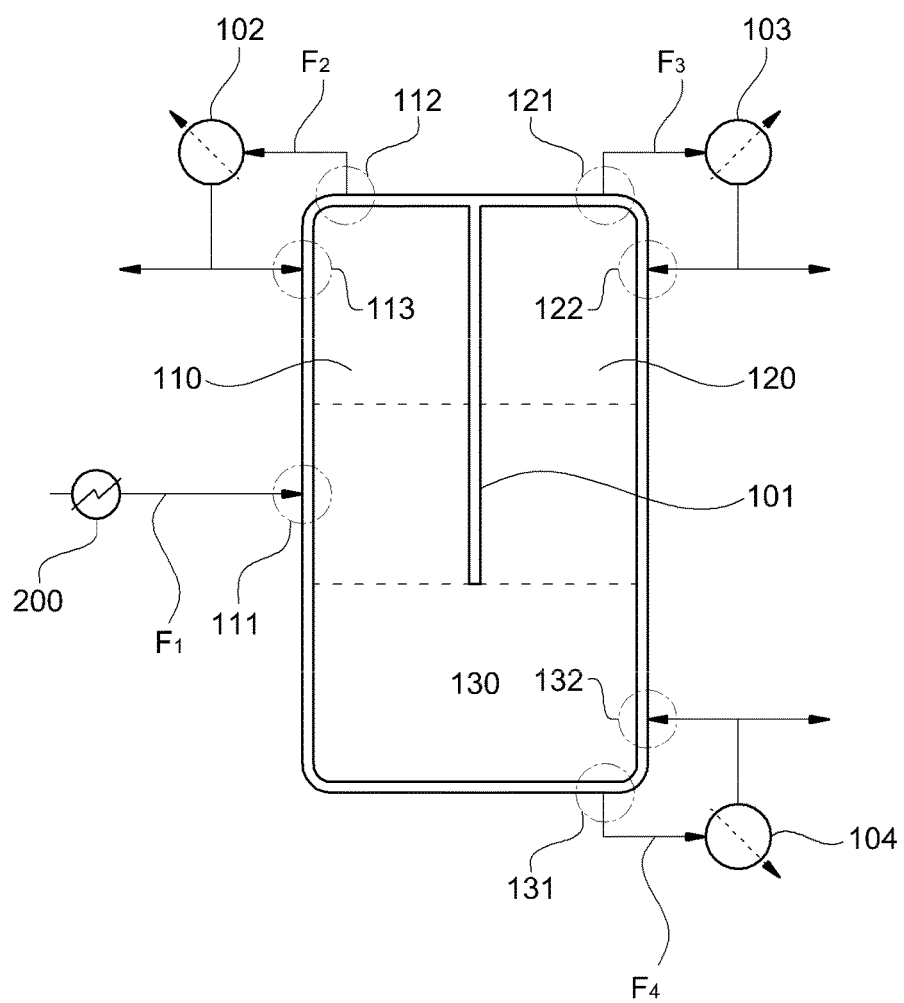

[Fig. 15]
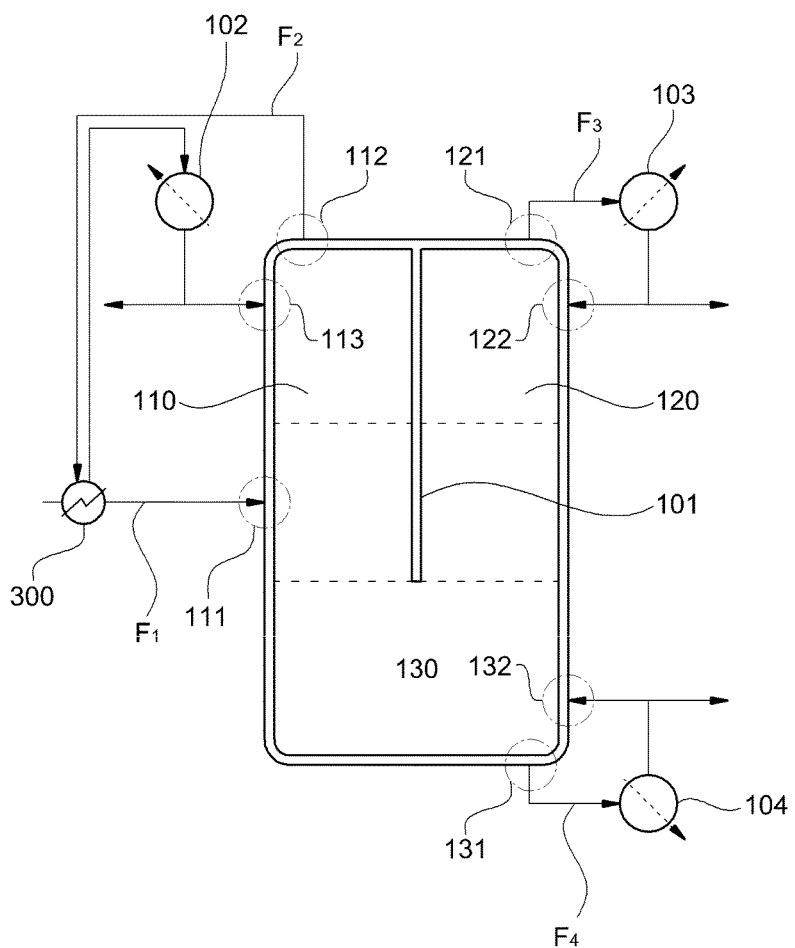

[Fig. 16]
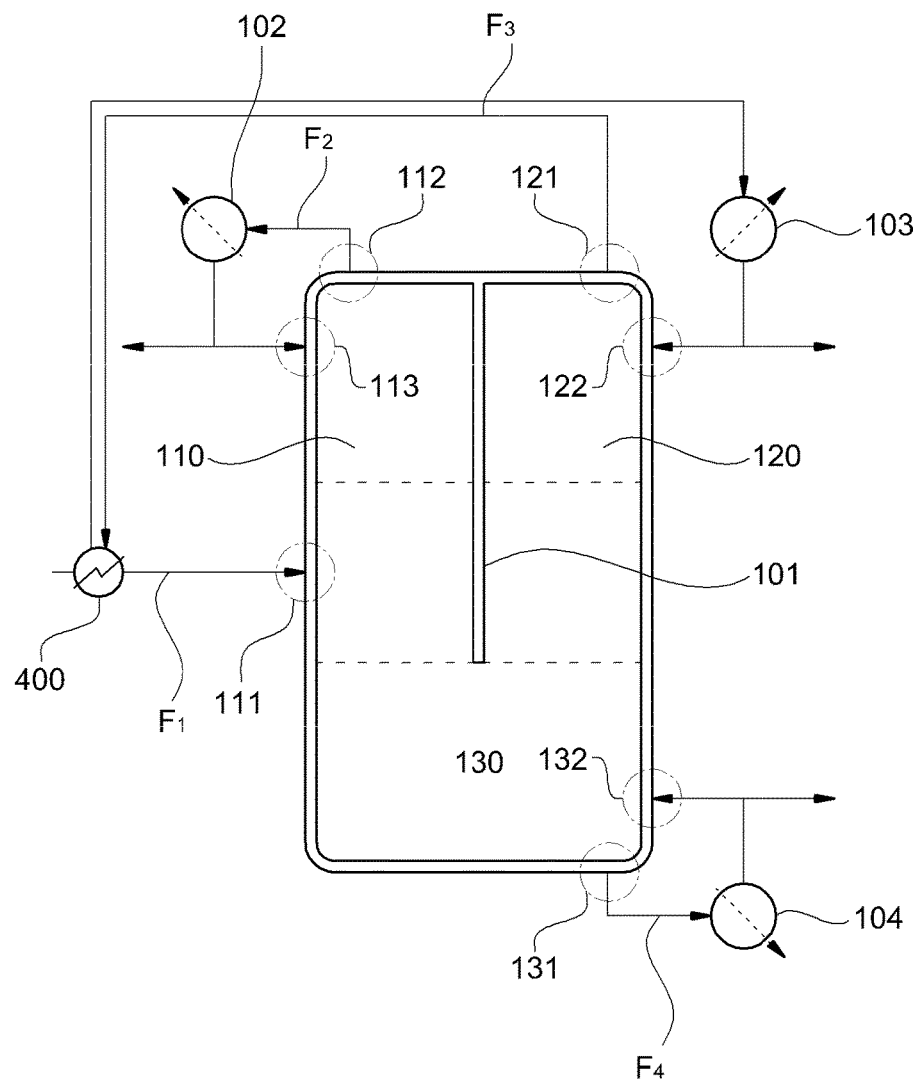

[Fig. 17]
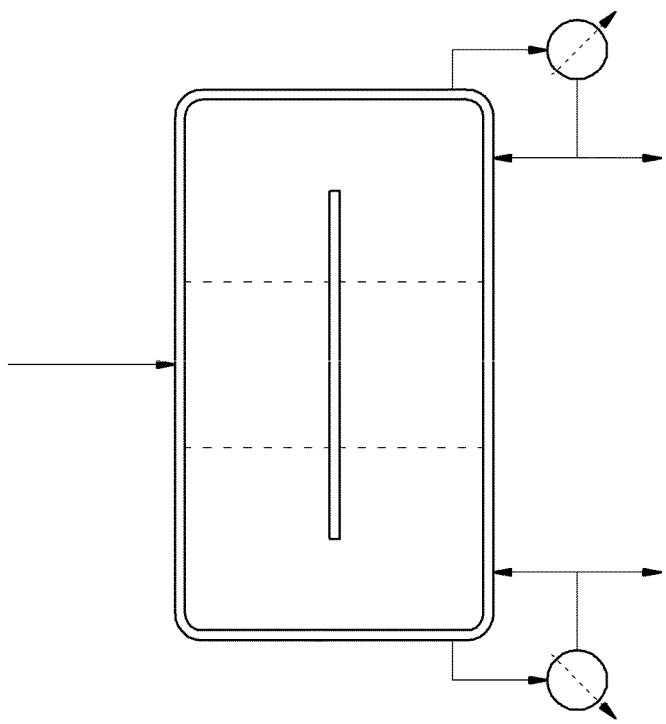
[Fig. 18]
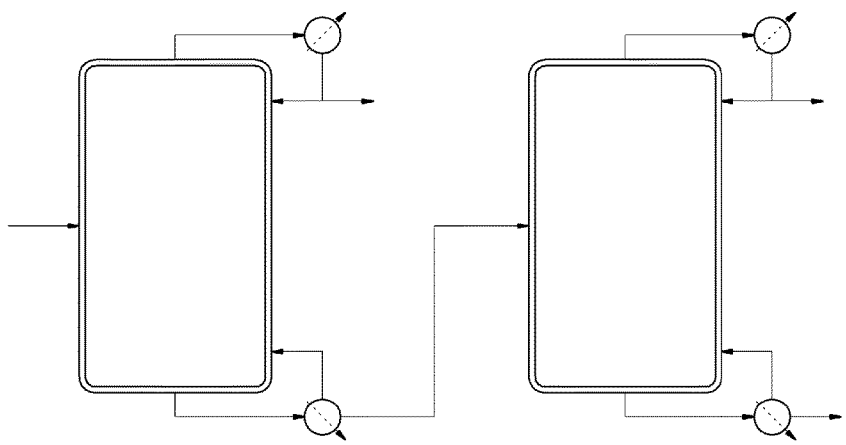

DIVIDED WALL DISTILLATION COLUMN

This application is a National Stage Application of International Application No. PCT/KR2014/006574, filed on Jul. 18, 2014, which claims the benefit of Korean Patent Application No. 10-2013-0084495, filed on Jul. 18, 2013, Korean Patent Application No. 10-2013-0084496, filed on Jul. 18, 2013, Korean Patent Application No. 10-2013-0106471, filed on Sep. 5, 2013, and Korean Patent Application No. 10-2014-0091328, filed on Jul. 18, 2014, all of which are hereby incorporated by reference in their entirety for all purposes as if fully set forth herein.

TECHNICAL FIELD

The present application relates to a divided wall distillation column and a method of separating 2-ethyl hexyl acrylate using the same.

BACKGROUND ART

Various raw materials including crude oil are a mixture of various materials, for example, various compounds. These raw materials can be generally divided into the respective compounds and then used. A representative process of separating the mixture is a distillation process.

For example, the mixture may be distilled by passing through one or more distillation columns. In the distillation process, a part of a flow or the entire flow may be fed back to the distillation columns after passing through a condenser or a reboiler. Through this process, high-purity compounds can be obtained. In general, a raw material including a material having three or more components can be divided into each component by passing through two or more distillation columns. For example, a low boiling point component can be primarily separated from the raw material at an upper part of a first distillation column, and an intermediate boiling point component and a high boiling point component can be separated from the raw material at upper and lower parts of a second distillation column connected to the first distillation column. In this case, remixing of intermediate boiling point components may occur in a lower area of the first distillation column. Thus, additional energy consumption may occur.

DISCLOSURE

Technical Problem

The present application is directed to providing a divided wall distillation column and a method of separating 2-ethyl hexyl acrylate with high purity using the divided wall distillation column.

Technical Solution

One aspect of the present application provides a divided wall distillation column. In the divided wall distillation column according to the present application, energy loss that occurs in a refinement process of a raw material including a mixture, for example, a compound represented by the following Formula 1 may be minimized. Since installation costs of a distillation apparatus can be reduced compared to a case where refinement is performed using two distillation columns, economic feasibility of the process can be enhanced.

Hereinafter, the divided wall distillation column according to the present application will be described with reference to the drawings. However, the drawings are just illustrative, and the scope of the distillation column is not limited to the attached drawings.

FIG. 1 is a view of a divided wall distillation column 100 according to an exemplary embodiment of the present application. In one example, the divided wall distillation column 100 is the divided wall distillation column 100 into which a raw material $F_1$ including the compound represented by the following Formula 1 is introduced and refined.

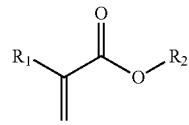

[Formula 1]

in Formula 1, $R_1$ is hydrogen or an alkyl group having 1 to 10 carbon atoms, for example, 1 to 8, 1 to 6, or 1 to 4 carbon atoms, and $R_2$ is a linear or branched form alkyl group having 1 to 24 carbon atoms, for example, 1 to 20, 1 to 16, 1 to 12, or 1 to 8 carbon atoms.

In one example, a component of Formula 1 is not specifically limited and may be any one of compounds that satisfy Formula 1. For example, the component of Formula 1 may be butyl acrylate, methyl acrylate, methyl methacrylate, 2-ethyl hexyl acrylate, acrylic acid, ethylene glycol, butyl alcohol, methyl alcohol, or isopropyl alcohol, and preferably, 2-ethyl hexyl acrylate.

The divided wall distillation column 100 is an apparatus invented to distillate the raw material $F_1$ including three components, i.e., a low boiling point component, an intermediate boiling point component, and a high boiling point component and is similar to a so-called thermally coupled distillation column (Petlyuk column), in a thermodynamic aspect. The thermally coupled distillation column is configured to primarily separate a low boiling point material and a high boiling point material using a pre-separator and to separate the low boiling point material, an intermediate boiling point material, and a high boiling point material, respectively, using a main separator. In this regard, in the divided wall distillation column 100, a divided wall is installed in a column so that the pre-separator may be integrated into the main separator.

In one example, the divided wall distillation column 100 according to the present application may have a structure illustrated in FIG. 1. As illustrated in FIG. 1, the divided wall distillation column 100 according to an exemplary embodiment of the present application is divided by a divided wall 101 and includes a first condenser 102, a second condenser 103, and a reboiler 104. Also, the divided wall distillation column 100 may have a structure in which the divided wall 101 is in contact with a column top of the divided wall distillation column 100 and is spaced apart from a column bottom of the divided wall distillation column 100. Thus, an inside of the divided wall distillation column 100 may be classified into a first area 110 and a second area 120 that are divided by the divided wall 101, and a third area 130 in which the divided wall 101 is not placed and which is formed at bottom of the first area 110 and the second area 120, as divided by virtual dotted lines of FIG. 1. Also, the first area 110, the second area 120, and the third area 130 may be respectively divided into upper and lower parts.

Thus, the inside of the divided wall distillation column 100 according to the present application may be classified into an upper part of the first area 110, a lower part of the first area 110, an upper part of the second area 120, a lower part of the second area 120, an upper part of the third area 130, and a lower part of the third area 130. The divided wall distillation column 100 according to the present application has a structure in which the divided wall 101 is in contact with the column top of the divided wall distillation column 100 so that the upper part of the first area 110 and the upper part of the second area 120 may be separated or isolated from each other by the divided wall 101. Thus, a flow from the upper part of the first area 110 and a flow from the upper part of the second area 120 may be prevented from being mixed with each other.

The term ⌈upper part and lower part of the first area⌋ used herein refers to a relatively upper part and a relatively lower part within the first area 110, respectively. For example, when the first area 110 divided by the divided wall 101 in the divided wall distillation column 100 is divided into two parts in a height or length direction of the column 100, ⌈an upper part and a lower part of the first area⌋ may refer to an upper part and a lower part of the two divided parts within the first area 110, respectively. Similarly, the term ⌈upper part and lower part of the second area⌋ refers to a relatively upper part and a relatively lower part within the second area 120, respectively, and may refer to an upper part and a lower part of two divided parts within the second area 120, which are formed when the second area 120 divided by the divided wall 101 in the divided wall distillation column 100 is divided into two parts in the height or length direction of the column 100. Also, the term ⌈an upper part and a lower part of the third area⌋ refers to a relatively upper part and a relatively lower part within the third area 130, respectively, and may refer to an upper part and a lower part of two divided parts within the third area 130, which are formed when the third area 130 divided by the divided wall 101 in the divided wall distillation column 100 is divided into two parts in the height or length direction of the column 100.

Also, the term ⌈separation or isolation⌋ used herein means that a flow in each area independently flows or exists in an area divided by the divided wall 101. For example, a fluid flow in the first area 110 of the divided wall distillation column 100 is discharged from the upper part of the first area 110 or the lower part of the first area 110 and flows into the third area 130, and a fluid flow in the second area 120 is discharged from the upper part of the second area 120 or the lower part of the second area 120 and flows into the third area 130. Thus, the flow in the first area 110 and the flow in the second area 120 may not be mixed with each other, may be necessarily mixed only in the third area 130 and thus may flow independently.

In one example, the divided wall distillation column 100 may include a raw material inflow part 111 to which the raw material $F_1$ is supplied, a first upper product outflow part 112 from which a first outflow stream $F_2$ is discharged from the upper part of the first area 110 of the divided wall distillation column 100, a first upper reflux inflow part 113 in which a part of the first outflow stream $F_2$ or the entire first outflow stream $F_2$ is fed back to the divided wall distillation column 100, a second upper product outflow part 121 from which a second outflow stream $F_3$ is discharged from the upper part of the second area 120 of the divided wall distillation column 100, a second upper reflux inflow part 122 in which a part of the second outflow stream $F_3$ or the entire second outflow stream $F_3$ is fed back to the divided wall distillation column 100, a third lower product outflow part 131 from which a third outflow stream $F_4$ is discharged from the lower part of the third area 130 of the divided wall distillation column 100, and a third lower reflux inflow part 132 in which a part of the third outflow stream $F_4$ or the entire third outflow stream $F_4$ is fed back to the divided wall distillation column 100. For example, the raw material inflow part 111 may be placed in the first area 110 of the divided wall distillation column 100, preferably, in the lower part of the first area 110 of the divided wall distillation column 100. Also, the first upper product outflow part 112 and the first upper reflux inflow part 113 may be placed at the upper part of the first area 110 of the divided wall distillation column 100, and preferably, the first upper product outflow part 112 may be placed on the column top of the first area 110 of the divided wall distillation column 100. Also, the second upper product outflow part 121 and the second upper reflux inflow part 122 may be placed at the upper part of the second area 120 of the divided wall distillation column 100, and preferably, the second upper product outflow part 121 may be placed on the column top of the second area 120 of the divided wall distillation column 100. Furthermore, the third lower product outflow part 131 and the third lower reflux inflow part 132 may be placed at the lower part of the third area 130 of the divided wall distillation column 100, and preferably, the third lower product outflow part 131 may be placed on the column bottom of the third area 130 of the divided wall distillation column 100. ⌈Column top⌋ of the divided wall distillation column 100 refers to a top of a column of the divided wall distillation column 100 and may be included in an upper part of the divided wall distillation column 100 described above, and ⌈column bottom⌋ of the divided wall distillation column 100 refers to a bottom of the column of the divided wall distillation column 100 and may be included in a lower part of the divided wall distillation column 100 described above.

For example, a material having a relatively low boiling point from among components included in the raw material $F_1$ may be discharged from the first upper product outflow part 112 of the divided wall distillation column 100, and a material having a relatively intermediate boiling point from among the components included in the raw material $F_1$ may be discharged from the second upper product outflow part 121, and a material having a relatively high boiling point from among the components included in the raw material $F_1$ may be discharged from the third lower product outflow part 131. The term ⌈low boiling point flow⌋ used herein refers to a flow that is discharged from the upper part of the first area 110 of the divided wall distillation column 100 and is enriched with a low boiling point component with a relatively low boiling point from among components of the raw material $F_1$ including three components, such as a low boiling point component, an intermediate boiling point component, and a high boiling point component. The term ⌈high boiling point flow⌋ used herein refers to a flow that is discharged from the lower part of the third area 130 of the divided wall distillation column 100 and is enriched with a high boiling point component with a relatively high boiling point from among the components of the raw material $F_1$ including three components, such as the low boiling point component, the intermediate boiling point component, and the high boiling point component. Also, the term ⌈intermediate boiling point flow⌋ used herein refers to a flow that is discharged from the upper part of the second area 120 of the divided wall distillation column 100 and is enriched with an intermediate boiling point component with a boiling point between the low boiling point component and the high boiling point component from among the components of the raw material $F_1$ including three components, such as the low boiling point component, the intermediate boiling point component, and the high boiling point component. The ⌈enriched flow⌋ refers to a flow in which the content of the low boiling point component included in the flow discharged from the upper part of the first area 110, the content of the intermediate boiling point component included in the flow discharged from the upper part of the second area 120 and the content of the high boiling point component included in the flow discharged from the lower part of the third area 130 are higher than the content of the low boiling point component, the content of the high boiling point component and the content of the intermediate boiling point component included in the raw material $F_1$. For example, the ⌈enriched flow⌋ may refer to a flow in which the content of the low boiling point component included in the first outflow stream discharged from the upper part of the first area 110 of the divided wall distillation column 100, the content of the intermediate boiling point component included in the second outflow stream discharged from the upper part of the second area 120 and the content of the high boiling point component included in the third outflow stream discharged from the lower part of the third area 130 are 50 parts by weight or higher, 80 parts by weight or higher, 90 parts by weight or higher, 95 parts by weight or higher, or 99 parts by weight or higher, based on 100 parts by weight of the content of the low boiling point component, the content of the high boiling point component and the content of the intermediate boiling point component included in the raw material $F_1$. In the present specification, the low boiling point flow and the first outflow stream $F_2$ may be used with an identical meaning, and the intermediate boiling point flow and the second outflow stream $F_3$ may be used with an identical meaning, and the high boiling point flow and the third outflow stream $F_4$ may be used with an identical meaning.

In order to perform a separation process on the raw material $F_1$ including three components, i.e., the low boiling point component, the intermediate boiling point component, and the high boiling point component, the raw material $F_1$ may be introduced into the first area 110 of the divided wall distillation column 100, as illustrated in FIG. 1. In one example, the raw material $F_1$ may be introduced into the raw material inflow part 111 of the lower part of the first area 110, and the low boiling point component having a relatively low boiling point from among the components included in the raw material $F_1$ is discharged from the upper part of the first area 110, and the intermediate boiling point component and the high boiling point component having relatively high boiling points are introduced into the third area 130. The flow of the intermediate boiling point component having a relatively low boiling point of the flow introduced into the third area 130 is introduced into the second area 120, and the flow of the high boiling point component having a relatively high boiling point of the flow introduced into the third area 130 is discharged from the lower part of the third area 130. Also, a component having a relatively low boiling point of the flow introduced into the second area 120 is discharged from the upper part of the second area 120. In detail, the raw material $F_1$ introduced into the raw material inflow part 111 placed at the lower part of the first area 110 of the divided wall distillation column 100 is separated into a component having a relatively low boiling point and a component having a relatively high boiling point in the first area 110, and the low boiling point component from among three components of the raw material $F_1$ is discharged as the first outflow stream $F_2$ from the first upper product outflow part 112 of the divided wall distillation column 100, and the intermediate boiling point component and the high boiling point component having relatively high boiling points are introduced into the third area 130. The components introduced into the third area 130 are again separated into a component having a relatively low boiling point and a component having a relatively high boiling point, and the component having a relatively high boiling point from among the components introduced into the third area 130, i.e., the high boiling point component from among three components of the raw material $F_1$ is discharged as the third outflow stream $F_4$ from the third lower product outflow part 131 of the divided wall distillation column 100. Also, a significant amount of the component having a relatively low boiling point from among the components introduced into the third area 130, i.e., the significant amount of an intermediate boiling point component from among three components of the raw material $F_1$ is introduced into the second area, is separated into a component having a relatively low boiling point and a component having a relatively high boiling point from among components introduced into the second area 120, and an amount of the intermediate boiling point component may also be reintroduced into the first area 110.

In one example, if the raw material $F_1$ including 2-ethyl hexyl acrylate is introduced into the divided wall distillation column 100, the first outflow stream $F_2$ may be discharged from the first upper product outflow part 112 placed on the column top of the first area 110 of the divided wall distillation column 100, and a part of the first outflow stream $F_2$ may be fed back to the first upper reflux inflow part 113 of the divided wall distillation column 100 via the first condenser 102, and the other part of the first outflow stream $F_2$ may be stored as a product. Also, the third outflow stream $F_4$ may be discharged from the third lower product outflow part 131 placed on the column bottom of the third area 130 of the divided wall distillation column 100, and a part of the third outflow stream $F_4$ may be fed back to the third lower reflux inflow part 132 of the divided wall distillation column 100 via the reboiler 104, and the other part of the third outflow stream $F_4$ may be stored as a product. Furthermore, the second outflow stream $F_3$ including 2-ethyl hexyl acrylate that is a relatively intermediate boiling point component from among the components of the raw material $F_1$ may be discharged as the second outflow stream $F_3$ from the second upper product outflow part 121 placed on the column top of the second area 120 of the divided wall distillation column 100, and a part of the second outflow stream $F_3$ may be fed back to the second upper reflux inflow part 122 of the divided wall distillation column 100 via the second condenser 103, and the other part of the second outflow stream $F_3$ may be stored as a product. The ⌈condenser⌋ is a device that is installed separate from the distillation column and may be a device for cooling the flow discharged from the divided wall distillation column 100 by contact with cooling water introduced from the outside. In detail, the condenser may cool the flow discharged from the divided wall distillation column 100 using sensible heat of the cooling water. In one example, the divided wall distillation column 100 includes the first condenser 102 and the second condenser 103. For example, the first condenser 102 may be a device that condenses the first outflow stream $F_2$ discharged from the upper part of the first area 110 of the divided wall distillation column 100, and the second condenser 103 may be a device that condenses the second outflow stream $F_3$ discharged from the upper part of the second area 120 of the divided wall distillation column 100. Also, the ⌈reboiler⌋ is a heating device installed at an outside of the distillation column and may be a device for heating and vaporizing a flow having a high boiling point discharged from the divided wall distillation column 100. For example, the reboiler 104 may be a device that heats the third outflow stream $F_4$ discharged from the lower part of the third area 130 of the divided wall distillation column 100.

When the raw material $F_1$ is separated, as described above, the temperature of the first outflow stream $F_2$ may be 80 to 115° C., 85 to 100° C., or 90 to 130° C., and the temperature of the second outflow stream $F_3$ may be 100 to 130° C., 120 to 125° C., or 108 to 120° C., and the temperature of the third outflow stream $F_4$ may be 120 to 160° C., 130 to 155° C., or 140 to 147° C. Also, a reflux ratio of the first outflow stream $F_2$ fed back to the upper part of the first area 110 of the divided wall distillation column 100 with respect to the first outflow stream $F_2$ may be 1 to 10, and preferably, 1.2 to 7.0 or 1.5 to 4.5, in a thermodynamic aspect. A reflux ratio of the second outflow stream $F_3$ fed back to the upper part of the second area 120 of the divided wall distillation column 100 with respect to the second outflow stream $F_3$ may be 0.01 to 5.0, and preferably, 0.05 to 1.0 or 0.1 to 2.0, in the thermodynamic aspect. Also, a reflux ratio of the third outflow stream $F_4$ fed back to the lower part of the third area 130 of the divided wall distillation column 100 with respect to the third outflow stream $F_4$ may be 1 to 30, and preferably, 5 to 25 or 10 to 20, in the thermodynamic aspect. The term ⌈reflux ratio⌋ used herein refers to a ratio of a fed-back flow with respect to a flow discharged from the distillation column 100.

In one embodiment of the present application, one or more of the raw material inflow part 111, the first upper reflux inflow part 113, the second upper reflux inflow part 122, and the third lower reflux inflow part 132 of the divided wall distillation column 100 may be configured as two or more openings that are placed to be spaced apart from each other. Thus, channeling that occurs in the refinement process of the raw material $F_1$ is prevented so that energy loss may be minimized and economic feasibility of the process may be enhanced. In the present specification, ⌈channeling⌋ refers to a phenomenon in which contact between vapor and a liquid mixture in the distillation column is not smooth, or a displacement phenomenon of liquid in which a flow of a fluid is shifted to a particular portion of a wall surface in the divided wall distillation column. Channeling causes separation efficiency of the raw material $F_1$ to be greatly reduced, and additional consumption of energy.

In one example, in order to prevent channeling, two or more openings may be placed so that the flow introduced into or discharged from the divided wall distillation column 100 may be introduced or discharged in two or more directions. For example, the first area 110 of the divided wall distillation column 100 may include two or more first small areas 110 in which a horizontal cross sectional area of the distillation column 100 is equally divided. FIG. 2 is a view of a cross section parallel to the ground surface of the distillation column 100. As illustrated in FIG. 2, the divided wall distillation column 100 is divided into a first area 110 and a second area 120 divided by the divided wall 101. The first area 110 may include an arbitrary small area in which the horizontal cross section of the distillation column 100 is divided by an equal width, for example, a plurality of first small areas 110a and 110b. The second area 120 may also include a plurality of arbitrary second small areas 120a and 120b in which the horizontal cross section of the distillation column 100 is divided by the equal width. Preferably, the plurality of first small areas 110a and 110b and the plurality of second small areas 120a and 120b may be areas in which horizontal cross sections of the first area 110 and the second area 120 are divided by equal widths.

In one example, one or more of the raw material inflow part 111 and the first upper reflux inflow part 113 of the first area 110 of the distilled wall distillation column 100 may be formed as two or more openings that are placed to be spaced apart from each other. In this case, the two or more openings may be respectively placed in two or more first small areas. ⌈Respectively placing⌋ two or more openings may mean that one opening is placed in one small area of the plurality of small areas equally divided by the number of the openings. FIG. 3 is a view of a cross section parallel to the ground surface of the upper part of the distillation column 100 according to the present application in which two openings are formed. For example, as divided by virtual dotted lines in FIG. 3, the first area 110 may include two, equal, first small areas 110a and 110b. When one or more of the raw material inflow part 111 and the first upper reflux inflow part 113 of the divided wall distillation column 100 are formed as two openings placed to be spaced apart from each other, one opening is placed in one small area 110a of two first small areas 110a and 110b, and the other one opening is placed in the other one small area 110b adjacent to the small area 110a in which one opening is placed, so that one opening may be placed in each area.

In the divided wall distillation column 100 in which the raw material inflow part 111 and the first upper reflux inflow part 113 are formed as one opening, the raw material $F_1$ or a reflux flow is supplied only in one direction. In this case, channeling may occur. However, when one or more of the raw material inflow part 111 and the first upper reflux inflow part 113 of the divided wall distillation column 100 are formed as two or more openings, the raw material $F_1$ or the reflux flow is equally introduced in two or more directions so that channeling may be prevented.

In the divided wall distillation column 100 according to the present application, the position of each opening, the flow rate and direction of each flow are adjusted according to the number of openings (two or more) so that channeling may be effectively suppressed. For example, when one or more of the raw material inflow part 111 and the first upper reflux inflow part 113 of the divided wall distillation column 100 are formed as two or more openings, as described above, two raw material inflow parts 111 and the first upper reflux inflow part 113 may be placed in the first small areas 110a and 110b, respectively, in which the cross section parallel to the ground surface of the first area 110 is divided equally into two parts. In this case, an angle formed by an extension line that extends from one of two openings toward the center of the distillation column 100 and an extension line that extends from the other one of the two openings toward the center of the distillation column 100 may be 85° to 95°, 87° to 93°, or 89° to 91°. The angle may be adjusted to the above range so that blocking of channeling may be maximized. Also, in this case, all directions of vector components of the flow of each raw material $F_1$ introduced through two raw material inflow parts 111 may be directed toward a central point of the cross section parallel to the ground surface of the distillation column 100. For example, introduction velocity vector components projected onto the cross section of each raw material flow may be symmetrical with respect to each other based on a plane 1011 that is perpendicular to the divided wall 101 that passes through the central point of the cross section parallel to the ground surface of the distillation column 100. Likewise, all directions of vector components of each reflux flow introduced through two first upper reflux inflow parts 113 may be directed toward the central point of the cross section 100 parallel to the ground surface of the distillation column. For example, introduction velocity vector components projected onto the cross section of each reflux flow may be symmetrical with respect to each other based on the plane 1011 that is perpendicular to the divided wall 101 that passes through the central point of the cross section parallel to the ground surface of the distillation column 100. In the present specification, ⌈introduction velocity vector components projected onto the cross section⌋ refers to vector components projected onto the cross section of the divided wall distillation column 100 in which an introduction velocity (distance per unit time) vector through each inflow part is projected onto the cross section parallel to the ground surface of the divided wall distillation column 100. Also, in this case, the flow rate and introduction velocity of the flow introduced into each of the two openings are equally adjusted so that the occurrence of channeling may be substantially prevented.

FIG. 4 is a view of a cross section parallel to the ground surface of the upper part of the divided wall distillation column 100 according to the present application in which three openings are formed. As illustrated in FIG. 4, for example, one or more of the raw material inflow part 111 and the first upper reflux inflow part 113 of the divided wall distillation column 100 may be formed as three openings placed to be spaced apart from each other. The three openings may be respectively placed in first small areas 110a, 110b, and 110c in which the cross section parallel to the ground surface of the first area 110 is equally divided into three parts. In this case, an angle formed by an extension line that extends from one of the three openings of the divided wall distillation column 100 toward the center of the distillation column 100 and an extension line that extends from an opening adjacent to the one opening toward the center of the distillation column 100 may be 55° to 65°, 57° to 63°, or 59° to 61°. The angle is adjusted to the above range so that blocking of channeling may be maximized. Also, in this case, the flow rate and introduction velocity of the flow introduced into each of the three openings are equally adjusted so that the occurrence of channeling may be substantially prevented.

FIG. 5 is a view of a cross section parallel to the ground surface of the divided wall distillation column 100 in which four openings are formed. As illustrated in FIG. 5, one or more of the raw material inflow part 111 and the first upper reflux inflow part 113 of the divided wall distillation column 100 may be formed as four openings placed to be spaced apart from each other. The four openings may be respectively placed in first small areas 110a, 110b, 110c, and 110d in which the cross section parallel to the ground surface of the first area 110 is equally divided into four parts. In this case, an angle formed by an extension line that extends from one of the four openings of the divided wall distillation column 100 toward the center of the distillation column 100 and an extension line that extends from an opening adjacent to the one opening toward the center of the distillation column 100 may be 40° to 50°, 42° to 48°, or 44° to 46°. The angle is adjusted in the above range so that blocking of channeling may be maximized. Also, in this case, the flow rate and introduction velocity of the flow introduced into each of the four openings are equally adjusted so that the occurrence of channeling may be substantially prevented.

In one embodiment, the raw material inflow part 111 of the divided wall distillation column 100 may be formed as two or more openings placed to be spaced apart from each other. Two or more openings may be respectively placed in two or more first small areas in which the cross section parallel to the ground surface of the distillation column 100 is equally divided, preferably, the horizontal cross-sectional area of the first area 110 is divided by an equal width. In the divided wall distillation column 100 in which the raw material inflow part 111 is formed as one opening, a flow of liquid may not equally drop into a lower area of a supply stage of the divided wall distillation column 100, and channeling may occur. Thus, separation efficiency of the raw material $F_1$ may be lowered. However, when the raw material inflow part 111 of the divided wall distillation column 100 is formed as two or more openings, the flow of liquid that drops into a lower part of a raw material supply stage of the divided wall distillation column 100 may be equally maintained, and channeling is suppressed so that the raw material $F_1$ may be efficiently separated. In this case, two or more openings may be placed at the same stage in the first area 110. Thus, the raw material $F_1$ introduced into two or more openings is introduced so that a hydraulic flow may be smooth and channeling may be effectively prevented. For example, two or more raw material inflow parts 111 may be placed at the same stage of the lower part of the first area 110 of the divided wall distillation column 100. In the divided wall distillation column 100 having a theoretical number of 30 to 80 stages, 40 to 70 stages, preferably, 45 to 60 stages, the raw material inflow part 111 formed as two or more openings may be placed in 5 to 30 stages, preferably, 5 to 25 stages, more particularly, 10 to 20 stages of the divided wall distillation column 100. Also, when the raw material $F_1$ with the same flow rate is introduced into the raw material inflow part 111 formed as two or more openings, blocking of channeling may be easily performed, and operation convenience of the distillation column increases so that the raw material $F_1$ may be separated with high efficiency.

In another embodiment, the first upper reflux inflow part 113 of the divided wall distillation column 100 may be formed as two or more openings placed to be spaced apart from each other. In this case, as described above, two or more openings in the raw material inflow part 111 may be respectively placed in two or more first small areas in which the cross section of the distillation column 100 parallel to the ground surface is equally divided, preferably, the horizontal cross section of the first area 110 of the divided wall distillation column 100 is equally divided. In the divided wall distillation column 100 in which the first upper reflux inflow part 113 is formed as one opening, a reflux flow of the first outflow stream $F_2$ discharged from the upper part of the first area 110 of the divided wall distillation column 100 is introduced into the divided wall distillation column 100 in one direction so that channeling may occur. Thus, separation efficiency of the raw material $F_1$ may be lowered. In this case, additional energy is consumed so as to maintain a low boiling point of the first outflow stream $F_2$. However, when the first upper reflux inflow part 113 of the divided wall distillation column 100 is formed as two or more openings, the reflux flow of the first outflow stream $F_2$ discharged from the upper part of the first area 110 of the divided wall distillation column 100 is introduced into the divided wall distillation column 100 in two or more directions so that channeling is suppressed and the raw material $F_1$ may be effectively separated. In one example, two or more first upper reflux inflow parts 113 may be placed at the same stage of the upper part of the first area 110 of the divided wall distillation column 100, preferably, in an uppermost stage of the first area 110. For example, in the divided wall distillation column 100 having a theoretical number of 30 to 80 stages, 40 to 70 stages, preferably, 45 to 60 stages, the first upper reflux inflow part 113 formed as two or more openings may be placed in the uppermost stage of the divided wall distillation column 100, for example, at a first stage of the divided wall distillation column 100.

A detailed description of the first upper reflux inflow part 113 formed as two or more openings is the same as that of raw material inflow part 111 formed as two or more openings and thus will be omitted.

In another embodiment of the present application, the second area 120 of the divided wall distillation column 100 may include a plurality of second small areas in which the horizontal cross section of the distillation column 100 is divided by an equal width, preferably, the horizontal cross section of the second area 120 is divided by an equal width. In this case, the second upper reflux inflow part 122 of the divided wall distillation column 100 may be formed as two or more openings placed to be spaced apart from each other. Two or more openings may be respectively placed in two or more second small areas. FIG. 6 is a view of a cross section parallel to the ground surface of the divided wall distillation column 100 in which two openings are formed. For example, as divided by virtual dotted lines in FIG. 6, the second area 120 may include two equal second small areas 120a and 120b. When the second upper reflux inflow part 122 of the divided wall distillation column 100 is formed as two openings placed to be spaced apart from each other, one opening may be placed in one small area 120a of two second small areas 120a and 120b, and the other one opening may be placed in the other one small area 120b adjacent to the small area 120a in which the one opening is placed, so that one opening may be placed in each area. In the divided wall distillation column 100 in which the second upper reflux inflow part 122 is formed as one opening, a reflux flow is supplied in only one direction. In this case, channeling may occur. Thus, separation efficiency of the raw material $F_1$ may be lowered. In this case, additional energy is consumed so as to maintain an intermediate boiling point of the second outflow stream $F_3$. However, when the second upper reflux inflow part 122 of the divided wall distillation column 100 is formed as two or more openings, the reflux flow is equally introduced in two or more directions so that channeling may be prevented.

In one direction, two or more second upper reflux inflow parts 122 may be placed at the same stage of the upper part of the second area 120 of the divided wall distillation column 100, preferably, in an uppermost stage of the second area 120. For example, in the divided wall distillation column 100 having a theoretical number of 30 to 80 stages, 40 to 70 stages, preferably, 45 to 60 stages, the second upper reflux inflow part 122 formed as two or more openings may be placed in the uppermost stage of the divided wall distillation column 100, for example, in the first stage of the divided wall distillation column 100.

A detailed description of the second upper reflux inflow part 122 formed as two or more openings is the same as that of the first upper reflux inflow part 113 formed as two or more openings and thus will be omitted.

In one embodiment, both the first upper reflux inflow part 113 and the second upper reflux inflow part 122 of the divided wall distillation column 100 are formed as two or more openings so that blocking of channeling that may occur due to the reflux flow may be maximized. An embodiment of the first upper reflux inflow part 113 and the second upper reflux inflow part 122 of the divided wall distillation column 100 described above may apply to an embodiment of the first upper product outflow part 112 and the second upper product outflow part 121 without any changes. A detailed description thereof is the same as above and thus will be omitted.

In still another embodiment of the present application, the third area 130 of the divided wall distillation column 100 may include a plurality of third small areas in which the horizontal cross section of the distillation column 100 is equally divided, preferably, the horizontal cross section of the third area 130 is divided by an equal width. In this case, the third lower reflux inflow part 132 of the divided wall distillation column 100 may be formed as two or more openings placed to be spaced apart from each other. Two or more openings may be respectively placed in two or more third small areas. FIG. 7 is a view of a cross section parallel to the ground surface of the lower part of the divided wall distillation column 100 according to the present application in which two openings are formed. For example, as divided by virtual dotted lines in FIG. 7, the third area 130 may include two equal third small areas, 130a and 130b. When the third lower reflux inflow part 132 of the divided wall distillation column 100 is formed as two openings placed to be spaced apart from each other, one opening is placed in one small area 130a of two third small areas 130a and 130b, and the other opening is placed in the other small area 130b adjacent to the small area 130a in which one opening is placed, so that one opening may be placed in each area. In the divided wall distillation column 100 in which the third lower reflux inflow part 132 is formed as one opening, the reflux flow is supplied in only one direction. In this case, channeling may occur. However, when the third lower reflux inflow part 132 of the divided wall distillation column 100 is formed as two or more openings, the reflux flow is equally introduced in two or more directions so that channeling may be prevented.

In one embodiment, the third lower reflux inflow part 132 of the divided wall distillation column 100 may be formed as two or more openings placed to be spaced apart from each other. Two or more openings may be placed in two or more third small areas in which the horizontal cross sectional area of the third area 130 of the divided wall distillation column 100 is equally divided. For example, in the divided wall distillation column 100 in which the third lower reflux inflow part 132 is formed as one opening, the third outflow stream $F_4$ discharged from the lower part of the third area 130 of the divided wall distillation column 100 is introduced into the divided wall distillation column 100 in one direction so that channeling may occur. Thus, separation efficiency of the raw material $F_1$ may be lowered. In this case, additional energy is consumed so as to maintain a high boiling point of the third outflow stream $F_4$. However, when the third lower reflux inflow part 132 is formed as two or more openings, the third outflow stream $F_4$ discharged from the lower part of the third area 130 of the divided wall distillation column 100 is fed back in two or more directions, and thus channeling is suppressed so that separation efficiency of the raw material $F_1$ may be maintained. In one embodiment, two or more third lower reflux inflow parts 132 may be placed at the same stage of the lower part of the third area 130 of the divided wall distillation column 100, preferably, in a lowermost stage of the third area 130. For example, in the divided wall distillation column 100 having a theoretical number of 30 to 80 stages, 40 to 70 stages, preferably, 45 to 60 stages, the third lower reflux inflow part 132 formed as two or more openings may be placed in the lowermost stage of the divided wall distillation column 100, for example, in an 80th stage, a 70th stage, or a 60th stage of the divided wall distillation column 100.

In the divided wall distillation column 100 according to the present application including the third lower reflux inflow part 132 formed as two or more openings, the position of each opening and the flow rate and direction of a flow introduced into each opening are adjusted according to the number of openings so that channeling may be effectively suppressed. For example, when the third lower reflux inflow part 132 of the divided wall distillation column 100 is formed as two openings, as described above, two third lower reflux inflow parts 132 may be respectively placed in two third small areas 130a and 130b in which the cross section parallel to the ground surface is equally divided. For example, as illustrated in FIG. 8, the third outflow stream $F_4$ may be respectively fed back to the third lower reflux inflow part 132 formed as two openings of the divided wall distillation column 100. Channeling that may occur when the third outflow stream $F_4$ is fed back in only one direction, may be efficiently suppressed. In this case, as illustrated in FIG. 9, an angle formed by an extension line that extends from one of two openings to the center of the distillation column 100 and an extension line that extends from the other one opening to the center of the distillation column 100 may be, for example, 175° to 185°, preferably, 177° to 183°, more preferably, 179° to 181°.

In another example, the third lower reflux inflow part 132 of the divided wall distillation column 100 may be formed as three openings. Three third lower reflux inflow parts 132 may be respectively placed in three third small areas 130a, 130b, and 130c in which cross sections parallel to the ground surface of three third lower reflux inflow parts 132 of the divided wall distillation column 100 are equally divided. In detail, as illustrated in FIG. 10, the third outflow stream $F_4$ may be fed back to the third lower reflux inflow part 132 formed as three openings of the divided wall distillation column 100. In this case, as illustrated in FIG. 11, an angle formed by an extension line that extends from one of three openings to the center of the distillation column 100 and an extension line that extends from the other two openings to the center of the distillation column 100 may be, for example, 115° to 125°, preferably, 117° to 123°, more preferably, 119° to 121°.

In another example, the third lower reflux inflow part 132 of the divided wall distillation column 100 may be formed as four openings. Four third lower reflux inflow parts 132 may be respectively placed in four three small areas 130a, 130b, 130c, and 130d in which a cross section parallel to the ground surface of the distillation column 100 is equally divided. Also, as illustrated in FIG. 12, the third outflow stream F4 may be fed back to the third lower reflux inflow part 132 formed as four openings of the divided wall distillation column 100. Channeling that may occur during reflux may be efficiently suppressed. In this case, as illustrated in FIG. 13, an angle formed by an extension line that extends from one of four openings to the center of the distillation column 100 and an extension line that extends from two openings adjacent to the one opening to the center of the distillation column 100 may be, for example, 85° to 95°, preferably, 87° to 93°, more preferably, 89° to 91°.

FIGS. 9, 11, and 13 are views of a cross section parallel to the ground surface of the lower part of the divided wall distillation column 100 according to an embodiment of the present application. As illustrated in FIGS. 9, 11, and 13, in the divided wall distillation column 100 according to the present application, all introduction velocity vector components projected onto the cross section parallel to the ground surface of the distillation column 100 may be directed toward a central point of the cross section. In detail, the flow rate and the size of an introduction velocity introduced through two or more openings are identical to each other, and a value obtained by adding values obtained by multiplying the flow rate F of a fluid flow and introduction velocity vector components projected onto the cross section may be 0 (zero). As described above, when the sum of multiplication of the flow rate of the fluid flow through two or more openings and the introduction velocity vector components projected onto the cross section is offset as 0 (zero), channeling caused by two or more fluid flows may be effectively blocked. The term ⌈flow rate (F)⌋ may refer to a flow rate (volume per unit time) introduced through each opening.

The above-described embodiment of the third lower reflux inflow part 132 of the divided wall distillation column 100 may apply to the third lower product outflow part 131 without any changes. A detailed description thereof is as described above and thus will be omitted.

FIG. 14 is a view of a divided wall distillation column according to an embodiment of the present application.

As illustrated in FIG. 14, a divided wall distillation column 100 according to an embodiment of the present application may include a heater 200 that preheats the raw material $F_1$.

The heater 200 may be placed in the previous stage of a portion into which a raw material $F_1$ of the divided wall distillation column 100 is introduced. The heater 200 may heat the raw material $F_1$ to be introduced into the divided wall distillation column 100. Thus, the divided wall distillation column 100 including the heater 200 may raise the temperature of the raw material $F_1$ before the raw material $F_1$ is introduced into the divided wall distillation column 100. Thus, loss of energy generated in the separation process of the raw material F1 may be minimized, and the size of the distillation column used in a refinement process may be minimized.

In one embodiment, the raw material F1 having the temperature of 20 to 40° C. may be heated by the heater 200 to the temperature of 50 to 110° C., 60 to 100° C., or 70 to 90° C. The preheated raw material $F_1$ may be introduced into the lower part of the first area 110 of the divided wall distillation column 100, and components included in the raw material $F_1$ may be separated into a first outflow stream $F_2$, a second outflow stream $F_3$, and a third outflow stream $F_4$ according to boiling points of the components. As described above, when the raw material $F_1$ is preheated using the heater 200, the raw material $F_1$ may be preheated using low pressure steam, and the preheated raw material $F_1$ is introduced into the divided wall distillation column 100 so that the consumption amount of high pressure steam used in the reboiler 104 to heat a partial flow of the third outflow stream $F_4$ fed-back into the lower part of the third area 130 of the divided wall distillation column 100 is reduced. A detailed description of a process of separating the raw material $F_1$ in the divided wall distillation column 100 is as described above and thus will be omitted.

Various well-known devices in the art that may raise the temperature of the raw material $F_1$ may be used as the heater 200. The heater 200 may be properly selected according to the type and temperature of a raw material to be separated but is not specifically limited.

FIG. 15 is a view of the divided wall distillation column 100 according to another embodiment of the present application.

As illustrated in FIG. 15, the divided wall distillation column 100 according to the embodiment of the present application may further include a first heat exchanger 300.

The first heat exchanger 300 may be placed at a front end of a first condenser 102 of the divided wall distillation column 100 so the raw material $F_1$ may heat-exchange with a part of the first outflow stream $F_2$ or the entire first outflow stream $F_2$. Also, the first heat exchanger 300 may be placed to be directly or indirectly connected to a pipe through which the first outflow stream $F_2$ of the divided wall distillation column 100 flows. In one example, the first heat exchanger 300 may be connected directly to the pipe through which the first outflow stream $F_2$ flows, thereby the raw material $F_1$ efficiently heat-exchanges with the first outflow stream $F_2$. For example, in the divided wall distillation column 100 that further includes the first heat exchanger 300, the first outflow stream $F_2$ passes through the first heat exchanger 300 and supplies heat to the first heat exchanger 300. In this case, the first outflow stream $F_2$ discharged from the divided wall distillation column 100 may be fed back into the divided wall distillation column 100 at a relatively low temperature. In this way, when the divided wall distillation column 100 including the first heat exchanger 300 is used, the amount of heat used to condense the first outflow stream $F_2$ discharged from the upper part of the first area 110 may be reduced. Thus, the amount of cooling water used in a condensation process using the first condenser 102 is reduced so that costs used in the condensation process may be reduced. Also, the first heat exchanger 300 facilitates the raw material $F_1$ to heat-exchange with a part of the first outflow stream $F_2$ having a relatively high temperature or the entire first outflow stream $F_2$ before the raw material $F_1$ is introduced into the divided wall distillation column 100, thereby raising the temperature of the raw material $F_1$. Thus, the consumption amount of steam used in the reboiler 104 to heat a partial flow of the third outflow stream $F_4$ discharged from the divided wall distillation column 100 fed back into the lower part of the third area 130 may be reduced. Also, latent heat generated in high temperature steam is used so that the temperature of the raw material may be efficiently increased with smaller thermal energy compared to a case where sensible heat of liquid is used. In this way, waste heat to be discarded is used so that energy efficiency may be improved, the size of the distillation column used in a refinement process may be minimized and compounds may be separated with high purity.

For example, the raw material $F_1$ at the temperature of 20 to 40° C. may be heated by the first heat exchanger 300 to the temperature of 50 to 110° C., 60 to 100° C., or 70 to 90° C. The preheated raw material $F_1$ may be introduced into the lower part of the first area 110 of the divided wall distillation column 100. Also, the first outflow stream $F_2$ at the temperature of 80 to 115° C. that heat-exchanges with the raw material $F_1$ may pass through the first condenser 102 and then may be condensed at 25 to 40° C. and may be stored as a product or may be fed back into the upper part of the first area 110 of the divided wall distillation column 100.

FIG. 16 is a view of the divided wall distillation column 100 according to still another embodiment of the present application.

As illustrated in FIG. 16, the divided wall distillation column 100 according to the embodiment of the present application may further include a second heat exchanger 400. The second heat exchanger 400 may be placed in a front end of a second condenser 103 of the divided wall distillation column 100 so that the raw material $F_1$ heat-exchanges with a part of the second outflow stream $F_3$ or the entire second outflow stream $F_3$. Also, the second heat exchanger 400 may be placed to be directly or indirectly connected to a pipe through which the second outflow stream $F_3$ of the divided wall distillation column 100 flows. In one example, the second heat exchanger 400 is connected directly to the pipe through which the second outflow stream $F_3$ flows, thereby the raw material $F_1$ efficiently heat-exchanges with the second outflow stream $F_3$.

For example, in the divided wall distillation column 100 that further includes the second heat exchanger 400, the second outflow stream $F_3$ passes through the second heat exchanger 400 and supplies heat to the second heat exchanger 400. Thus, the second outflow stream $F_3$ may be fed back into the divided wall distillation column 100 at a relatively low temperature. Also, a part of the second outflow stream F3 having a relatively high temperature or the entire second outflow stream $F_3$ heat-exchanges with the raw material $F_1$ before the raw material $F_1$ is introduced into the divided wall distillation column 100, so that the temperature of the raw material $F_1$ may be increased. As described above, when the divided wall distillation column 100 including the second heat exchanger 400 is used, the amount of cooling water used in the second condenser 103 and the amount of steam used in the reboiler 104 may be reduced. A detailed description thereof is as described above and thus will be omitted.

For example, the raw material $F_1$ at the temperature of 20 to 40° C. may be heated by the second heat exchanger 400 to the temperature of 50 to 110° C., 60 to 120° C., or 90 to 110° C. The preheated raw material $F_1$ may be introduced into the lower part of the first area 110 of the divided wall distillation column 100. Also, the second outflow stream $F_3$ at the temperature of 100 to 130° C. that heat-exchanges with the raw material $F_1$ may pass through the second condenser 103 and then may be condensed at 40° C. to 95° C. and may be stored as a product or may be fed back into the upper part of the second area 120 of the divided wall distillation column 100.

The present application relates to a method of separating a raw material. For example, the method of separating the raw material may be performed by the distillation column 100 provided with the above-described divided wall.

The method of separating the raw material $F_1$ according to the present application includes refining the raw material $F_1$. Hereinafter, the term ⌈introducing⌋ or ⌈introduction⌋ is used in an identical meaning as an introducing operation, and the term ⌈refining⌋ or ⌈refinement⌋ is used in an identical meaning as a refining operation. In one example, the introducing operation is performed by introducing the raw material $F_1$ into the divided wall distillation column 100.

[Formula 1]

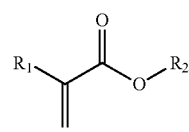

The raw material $F_1$ may include the compound of Formula 1, for example, butyl acrylate, methyl acrylate, methyl methacrylate, 2-ethyl hexyl acrylate, acrylic acid, ethylene glycol, butyl alcohol, methyl alcohol, or isopropyl alcohol, and preferably, 2-ethyl hexyl acrylate. A description of the raw material $F_1$ is as described above and thus will be omitted.

In the introducing operation of the raw material $F_1$, the raw material $F_1$ may be introduced into the divided wall distillation column 100 that is divided into the first area 110 and the second area 120 that are divided by the divided wall 101 and the third area 130 in which the divided wall 101 is not placed. For example, the raw material $F_1$ may be introduced into the lower part of the first area 110 of the divided wall distillation column 100. Also, in the refining operation, the raw material $F_1$ introduced into the divided wall distillation column 100 is separated into the first outflow stream $F_2$, the second outflow stream $F_3$, and the third outflow stream $F_4$. For example, in the refining operation, a flow having a relatively low boiling point of the introduced raw material $F_1$ may be discharged as the first outflow stream $F_2$ from the upper part of the first area 110, and an intermediate boiling point flow and a high boiling point flow having relatively high boiling points may be introduced into the third area 130. The flow of an intermediate boiling point component having a relatively low boiling point of the flow introduced into the third area 130 may be introduced into the second area 120, and the flow of a high boiling point component having a relatively high boiling point of the flow introduced into the third area 130 may be discharged as the third outflow stream $F_4$ in the third area 130. Also, a component having a relatively intermediate boiling point of the flow introduced into the second area 120 may be discharged as the second outflow stream $F_3$ in the second area 120. Furthermore, the flow discharged from the upper part of the first area 110 and the flow discharged from the upper part of the second area 120 may be prevented from being mixed by the divided wall 101 of the divided wall distillation column 100 so that costs required in a process may be reduced and a compound having high purity may be obtained. A detailed description of temperatures and reflux ratios of the first outflow stream $F_2$ discharged from the upper part of the first area 110 of the divided wall distillation column 100, the second outflow stream $F_3$ discharged from the upper part of the second area 120, and the third outflow stream $F_4$ discharged from the third area 130 is as described above in the divided wall distillation column 100 and thus will be omitted.

In addition, the method of separating the raw material according to the present application may further include preheating the raw material $F_1$ before introducing the raw material $F_1$ into the distillation column 100. Hereinafter, the term ⌜preheating⌟ or ⌜preheat⌟ is used in an identical meaning as a preheating operation. The preheating operation is performed before the above-described introducing operation, and the raw material $F_1$ may be heated before it is introduced into the lower part of the first area 110 of the divided wall distillation column 100 so that loss of energy generated in the separation process of the raw material $F_1$ may be minimized. In the preheating operation, the raw material $F_1$ introduced into the divided wall distillation column 100 may be preheated using an external heat source. In an exemplary preheating operation, the raw material $F_1$ may be heated using the heater 200. For example, the raw material $F_1$ is heated before it is introduced into the distillation column 100 using the heater 200, so that the consumption amount of heat used in the reboiler 104 to heat a partial flow of the third outflow stream $F_4$ fed back into the lower part of the third area 130 may be reduced. A detailed description of the heater 200 is as described above and thus will be omitted.

In one example, the preheating operation may include a flow discharged from the upper part of the first area 110 of the distillation column 100 and/or a flow discharged from the upper part of the second area 120 of the distillation column 100 heat-exchanging with the raw material $F_1$. For example, in the preheating operation, the first outflow stream $F_2$ discharged from the first area 110 of the distillation column 100 and/or the second outflow stream $F_3$ discharged from the second area 120 of the distillation column 100 supply heat by passing through the heat exchanger. Thus, the raw material $F_1$ having a low temperature introduced into the distillation column 100 may be heated using waste heat discharged in the separation process of the raw material $F_1$, and energy loss generated in the separation process may be minimized. Furthermore, the amount of cooling water used in the first condenser 102 and the amount of cooling water used in the second condenser 103 may be reduced before at least one of the first outflow stream $F_2$ and the second outflow stream $F_3$ of the divided wall distillation column 100 is respectively fed back into the distillation column 100. Also, the consumption amount of heat used in the reboiler 104 to heat a part of a flow or the entire flow of the third outflow stream $F_4$ fed back into the lower part of the third area 130 of the divided wall distillation column 100 may be reduced. In the method of separating the raw material, a detailed description of temperatures and reflux ratios of the raw material $F_1$ introduced into the divided wall distillation column 100, the first outflow stream $F_2$ discharged from the upper part of the first area 110, the second outflow stream $F_3$ discharged from the upper part of the second area 120, and the third outflow stream $F_4$ discharged from the third area 130 is as described above in the divided wall distillation column 100 and thus will be omitted.

In the divided wall distillation column 100 and the method of separating the raw material using the same according to the present application, the consumption amount of energy is reduced, and the size of the distillation column used in refinement of the raw material is minimized so that economic feasibility of the process may be enhanced.

Advantageous Effects

In a divided wall distillation column according to the present application, when a mixture having three or more components is separated, a material to be separated, for example, 2-ethyl hexyl acrylate may be separated with high purity, and energy reduction in a separation and refinement process of 2-ethyl hexyl acrylate can be promoted.

DESCRIPTION OF DRAWINGS

FIG. 1 is a view of a divided wall distillation column according to an embodiment of the present application.

FIGS. 2 through 13 are views of a cross section parallel to the ground surface of the divided wall distillation column according to embodiments of the present application.

FIG. 14 is a view of a divided wall distillation column according to an embodiment of the present application.

FIGS. 15 and 16 are views of the divided wall distillation column according to other embodiments of the present application.

FIG. 17 is a view of a conventional divided wall distillation column used in Comparative Example 1.

FIG. 18 is a view of a distillation device used in Comparative Example 2.

MODES OF THE INVENTION

Hereinafter, the present application will be described in more detail through Examples of the present application and Comparative examples that do not comply with the present application. However, the scope of the present application is not limited by the following Examples.

Example 1

2-ethyl hexyl acrylate was prepared using a divided wall distillation column of FIG. 1. In detail, a separation process was performed by introducing a raw material including 2-ethyl hexyl acrylate into the divided wall distillation column.

An operation pressure of an upper part of a first area of the divided wall distillation column was about 20 to 30 torr, and an operation temperature was about 90 to 105° C., and an operation pressure of an upper part of a second area was about 20 to 30 torr, and an operation temperature was about 108 to 120° C., and an operation pressure of a lower part of a third area was about 80 to 90 torr, and an operation temperature was about 140 to 147° C. In addition, a part of a high boiling point flow discharged from a lower part of the third area of the divided wall distillation column was fed back into the divided wall distillation column via a reboiler, and a part of a low boiling point flow and water discharged from the upper part of the first area was reintroduced into the divided wall distillation column via a first condenser, and the other part thereof was separated into a product. In this case, a reflux ratio of a first outflow stream of the divided wall distillation column was set to be 1.5 to 4.5, and a reflux ratio of a second outflow stream was set to be 0.1 to 2.0, and a reflux ratio of a third outflow stream was set to be 10 to 20.

Example 2

A process of separating a raw material was performed using the same method as that of Example 1 except for using a divided wall distillation column in which a raw material inflow part was formed as two openings and two raw material inflow parts were placed in a 15th stage of the divided wall distillation column having a theoretical number of 60 stages.

Example 3

A process of separating a raw material was performed using the same method as that of Example 1 except for using a divided wall distillation column in which a raw material inflow part and a first upper reflux inflow part were formed as two openings, two raw material inflow parts were placed in a 15th stage of the divided wall distillation column having a theoretical number of 60 stages and two first upper reflux inflow parts were placed in a first stage of the divided wall distillation column.

Example 4

A process of separating a raw material was performed using the same method as that of Example 1 except for using a divided wall distillation column in which a raw material inflow part and a second upper reflux inflow part were formed as two openings, two raw material inflow parts were placed in a 15th stage of the divided wall distillation column having a theoretical number of 60 stages and two second upper reflux inflow parts were placed in a first stage of the divided wall distillation column.

Example 5

A process of separating a raw material was performed using the same method as that of Example 1 except for using a divided wall distillation column in which a raw material inflow part and a third lower reflux inflow part were formed as two openings and two raw material inflow parts were placed in a 15 stage of the divided wall distillation column having a theoretical number of 60 stages and two third lower reflux inflow parts were placed in a 60th stages of the divided wall distillation column.

Example 6

A process of separating a raw material was performed using the same method as that of Example 1 except for using a divided wall distillation column in which a raw material inflow part, a first upper reflux inflow part, a second upper reflux inflow part and a third lower reflux inflow part were formed as two openings.

In this case, two raw material inflow parts were placed in a 15 stage of the divided wall distillation column having a theoretical number of 60 stages, and two first upper reflux inflow parts were placed in a first stage of the divided wall distillation column, and two second upper reflux inflow parts were placed in a first stage of the divided wall distillation column, and the third lower reflux inflow part was placed in a 60th stage of the divided wall distillation column.

Example 7

As illustrated in FIG. 14, a refinement process was performed using the same method as that of Example 1 except for installing a heater so that the temperature of a raw material of the divided wall distillation column may be increased before it is supplied into the divided wall distillation column. In this case, the temperature of the raw material to be introduced into the lower part of the first area of the divided wall distillation column was set to be about 70 to 90° C.

Example 8

As illustrated in FIG. 15, a raw material was separated using a divided wall distillation column including a first heat exchanger. That is, the raw material was refined using the same method as that of Example 1 except for performing heat-exchanging with the raw material introduced into the divided wall distillation column before a first outflow stream discharged from an upper part of a first area of the divided wall distillation column passes through a first condenser. In this case, the temperature of the raw material introduced into a lower part of the first area was set to be about 70 to 90° C.

Example 9

As illustrated in FIG. 16, a raw material was separated using a divided wall distillation column including a second heat exchanger. That is, the raw material was refined using the same method as that of Example 1 except for performing heat-exchanging with the raw material introduced into the divided wall distillation column before a second outflow stream discharged from an upper part of a second area of the divided wall distillation column passes through a second condenser. In this case, the temperature of the raw material introduced into a lower part of the first area was set to be about 90 to 110° C.

Comparative Example 1

As illustrated in FIG. 17, 2-ethyl hexyl acrylate was refined using a divided wall distillation column in which a divided wall is not in contact with a column top.

A part of a flow discharged from a column top area of the divided wall distillation column was fed back into an upper part of the divided wall distillation column via a condenser, and the other part of the flow was produced as a product. Also, a part of a flow discharged from a column bottom area of the divided wall distillation column was fed back into a lower part of the divided wall distillation column via a reboiler, and the other part of the flow was produced as a product.

In this case, a reflux ratio of a column top flow of the divided wall distillation column was set to be 2.5 to 5.5.

Comparative Example 2

As illustrated in FIG. 18, 2-ethyl hexyl acrylate was refined using a distillation device to which two distillation columns were connected.

A part of a low boiling point flow and water discharged from a column top area of a first distillation column was fed back into the first distillation column via a condenser, and the other part of the low boiling point flow and water was produced as a product. Also, a part of a flow discharged from a column bottom area of the first distillation column was again fed back into the column bottom area of the first distillation column via a reboiler, and the other part of the flow was introduced into a second distillation column.

An intermediate boiling point flow discharged from an upper part of a second distillation column was condensed using a condenser, and a part of the intermediate boiling point flow was fed back into a column top area of the second distillation column, and the other part of the intermediate boiling point flow was separated into a product, and a high boiling point flow discharged from a lower part of the second distillation column was fed back into a column bottom area of the second distillation column using a reboiler.

In this case, a reflux ratio of a column top flow of the second distillation column was set to be 0.2 to 1.2.

After 2-ethyl hexyl acrylate was refined according to the above Examples and Comparative Examples, it was shown in the following Table 1 whether channeling occurred in the refinement process.

TABLE 1

|  | Comparative example 1 | Example 1 | Example 2 | Example 3 | Example 4 | Example 5 | Example 6 |
| --- | --- | --- | --- | --- | --- | --- | --- |
| Degree of occurrence of channeling | o | o | x | x | x | x | x | x: channeling did not occur
o: channeling occurred

As shown in the above Table 1, channeling occurred in case of Comparative Example 1 in which a raw material was separated using a distilled wall distillation column having a general structure and when the raw material was separated according to Example 1 using a divided wall distillation column in which a raw material inflow part, a product outflow part and a reflux inflow part were formed as one opening. However, channeling did not occur during the separation process of the raw material in the cases of Examples 2 through 6 in which the raw material was refined using a divided wall distillation column in which one or more of the raw material inflow part, the product outflow part and the reflux inflow part were formed as two or more openings. Thus, when the raw material was refined using the divided wall distillation column including two or more inflow parts and outflow parts, separation efficiency of the raw material may be improved.

After 2-ethyl hexyl acrylate was refined according to the above examples and Comparative examples, the purity of 2-ethyl hexyl acrylate, the content of a low boiling point material in a product, and energy consumption amount were measured and were shown in the following Table 2.

TABLE 2

|  | Comparative example 1 | Comparative example 2 | Example 1 | Example 7 | Example 8 | Example 9 |
| --- | --- | --- | --- | --- | --- | --- |
| Product purity (parts by weight) | 99.95 | 99.95 | 99.96 | 99.96 | 99.96 | 99.96 |
| Content of low boiling point material in product | 10 ppm | 10 ppm | 3 ppb | 3 ppb | 3 ppb | 3 ppb |
| Energy consumption (Gcal/hr) | 0.92 | 1.2 | 0.91 | 0.91 | 0.84 | 0.81 |

As shown in the above Table 2, when 2-ethyl hexyl acrylate was refined according to Example 1 and Examples 7 through 9, 2-ethyl hexyl acrylate with high purity was obtained compared to a case where refinement was performed according to Comparative Examples 1 and 2.

In addition, total amounts of energy put in the refinement process according to Example 1 and Examples 7 through 9 were 0.91 Gcal/hr, 0.91 Gcal/hr, 0.84 Gcal/hr, and 0.81 Gcal/hr, respectively, and total energy consumption was greatly reduced compared to 0.92 Gcal/hr that was a total amount of energy put in the refinement process according to Comparative Example 1. That is, an energy reduction effect when 2-ethyl hexyl acrylate was separated using the divided wall distillation column according to the examples of the present application, was shown to be up to a maximum of 33% compared to the case of Comparative examples.

While the invention has been shown and described with reference to certain exemplary embodiments thereof, it will be understood by those skilled in the art that various changes in form and details may be made therein without departing from the spirit and scope of the invention as defined by the appended claims.

EXPLANATION OF REFERENCE NUMERALS $F_1$: raw material
$F_2$: first outflow stream
$F_3$: second outflow stream
$F_4$: third outflow stream
100: divided wall distillation column
101: divided wall
1011: plane perpendicular to the divided wall
102: first condenser
103: second condenser
104: reboiler
110: first area
110a, 110b, 110c, 110d: first small area
111: raw material inflow part
112: first upper product outflow part
113: first upper reflux inflow part
120: second area
120a, 120b: second small area
121: second upper product outflow part
122: second upper reflux inflow part
130: third area
130a, 130b, 130c: third small area
131: third lower product outflow part
132: third lower reflux inflow part
200: heater
300: first heat exchanger
400: second heat exchanger

The invention claimed is:

1. A dividing wall distillation column comprising a first condenser, a second condenser, a reboiler, and a distillation column provided with a dividing wall,
wherein the dividing wall distillation column is divided by the dividing wall into a first area and a second area, and wherein the dividing wall distillation column includes a third area in which the dividing wall is not placed and which is formed at bottom of the first area and the second area,
a raw material is introduced into the first area, and
the introduced raw material is divided into a first outflow stream that is discharged from an upper part of the first area, a second outflow stream that is discharged from a lower part of the first area, passes through the third area, is introduced into the second area and is discharged from an upper part of the second area, and a third outflow stream that is discharged from a lower part of the third area, and
a part of the first outflow stream passes through the first condenser and is fed back to the upper part of the first area, such that a first reflux ratio of the first outflow stream fed back to the upper part of the first area with respect to the first outflow stream is from 1 to 10,
a part of the second outflow stream passes through the second condenser and is fed back to the upper part of the second area, such that a second reflux ratio of the second outflow stream fed back to the upper part of the second area with respect to the second outflow stream is from 0.05 to 1.0, and
a part of the third outflow stream passes through the reboiler and is fed back to the lower part of the third area, such that a third reflux ratio of the third outflow stream fed back to the lower part of the third area with respect to the third outflow stream is from 1 to 30,
wherein at least one of the first outflow stream, the second outflow stream and the third outflow stream is formed by two or more small streams,
wherein the two or more small streams flow from two or more openings, and
wherein the two or more small streams join to form the at least one of the first outflow stream, the second outflow stream and the third outflow stream after being discharged through the two or more openings.

2. The dividing wall distillation column of claim 1, wherein the raw material comprises a compound of the following Formula 1:

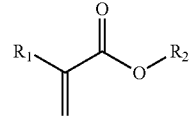

[Formula 1]

in Formula 1,
$R_1$ is hydrogen or an alkyl group having 1 to 10 carbon atoms, and $R_2$ is a linear or branched form alkyl group having 1 to 24 carbon atoms.

3. The dividing wall distillation column of claim 1, wherein the raw material is introduced into the lower part of the first area.

4. The dividing wall distillation column of claim 1, further comprising a heater that preheats the raw material before the raw material is introduced.

5. The dividing wall distillation column of claim 1, further comprising a first heat exchanger that is disposed at a front end of the first condenser for heat-exchanging with raw material and the first outflow stream.

6. The dividing wall distillation column of claim 5, further comprising a second heat exchanger that is disposed at a front end of the second condenser for heat-exchanging with the raw material and the second outflow stream.

7. The dividing wall distillation column of claim 1, wherein the first area comprises a raw material inflow part, a first upper product outflow part, and a first upper reflux inflow part, and the second area comprises a second upper product outflow part and a second upper reflux inflow part, and the third area comprises a third product outflow part and a third reflux inflow part, and
the raw material is introduced into the raw material inflow part, and the first outflow stream is discharged from the first upper product outflow part, and the second outflow stream is discharged from the second upper product outflow part, and the third outflow stream is discharged from the third product outflow part, and
a part of the first outflow stream is introduced into the first upper reflux inflow part, and a part of the second outflow stream is introduced into the second upper reflux inflow part, and a part of the third outflow stream is introduced into the third reflux inflow part, and
one or more of the raw material inflow part, the first upper reflux inflow part, the second upper reflux inflow part, and the third reflux inflow part are formed as two or more openings placed to be spaced apart from each other.

8. The dividing wall distillation column of claim 7, wherein the first area comprises two or more first small areas in which a horizontal cross-sectional area of the first area is equally divided, and one or more of the raw material inflow part and the first upper reflux inflow part are formed as two or more openings placed to be spaced apart from each other, and two or more openings are respectively placed in two or more first small areas.

9. The dividing wall distillation column of claim 8, wherein the first upper reflux inflow part is formed as two or more openings placed to be spaced apart from each other, and two or more openings are placed at a same stage in the first area.

10. The dividing wall distillation column of claim 8, wherein the raw material inflow part is formed as two or more openings placed to be spaced apart from each other, and two or more openings are placed at a same stage in the first area.

11. The dividing wall distillation column of claim 7, wherein the second area comprises two or more second small areas in which the horizontal cross-sectional area of the second area is equally divided, and the second upper reflux inflow part is formed as two or more openings placed to be spaced apart from each other, and two or more openings are respectively placed in two or more second small areas.

12. The dividing wall distillation column of claim 11, wherein the two or more openings are placed at a same stage in the second area.

13. The dividing wall distillation column of claim 7, wherein the third area comprises two or more third small areas in which the horizontal cross-sectional area of the distillation column is equally divided, and the third reflux inflow part is formed as two or more openings placed to be spaced apart from each other, and the two or more openings are respectively placed in two or more third small areas.

14. The dividing wall distillation column of claim 13, wherein the third reflux inflow part is formed as two or more openings placed to be spaced apart from each other, and the two or more openings are placed at a same stage in the third area.

15. A dividing wall distillation column comprising a first condenser, a second condenser, a reboiler, and a distillation column provided with a dividing wall,
wherein the dividing wall distillation column is divided by the dividing wall into a first area and a second area, and wherein the dividing wall distillation column includes a third area in which the dividing wall is not placed and which is formed at bottom of the first area and the second area,
a raw material is introduced into the first area, and
the introduced raw material is divided into a first outflow stream that is discharged from an upper part of the first area, a second outflow stream that is discharged from a lower part of the first area, passes through the third area, is introduced into the second area and is discharged from an upper part of the second area, and a third outflow stream that is discharged from a lower part of the third area, and
a part of the first outflow stream passes through the first condenser and is fed back to the upper part of the first area, such that a first reflux ratio of the first outflow stream fed back to the upper part of the first area with respect to the first outflow stream is from 1 to 10,
a part of the second outflow stream passes through the second condenser and is fed back to the upper part of the second area, such that a second reflux ratio of the second outflow stream fed back to the upper part of the second area with respect to the second outflow stream is from 0.05 to 1.0, and
a part of the third outflow stream passes through the reboiler and is fed back to the lower part of the third area, such that a third reflux ratio of the third outflow stream fed back to the lower part of the third area with respect to the third outflow stream is from 1 to 30,
wherein each of the second outflow stream and the third outflow stream are discharged in two or more directions through two or more openings.

* * * * *